United States Patent [19]

Manogue et al.

[11] Patent Number: 5,430,204

[45] Date of Patent: * Jul. 4, 1995

[54] HALOCARBON HYDROGENOLYSIS

[75] Inventors: William H. Manogue, Newark; V. N. Mallikarjuna Rao, Wilmington, both of Del.

[73] Assignee: E. I. du Pont de Nemours and Company, Wilmington, Del.

[*] Notice: The portion of the term of this patent subsequent to Nov. 15, 2011 has been disclaimed.

[21] Appl. No.: 242,503

[22] Filed: May 13, 1994

Related U.S. Application Data

[63] Continuation of Ser. No. 122,102, Sep. 16, 1993, Pat. No. 5,364,992, which is a continuation of Ser. No. 847,987, filed as PCT/US90/05637, Oct. 9, 1990, published as WO91/05752, May 2, 1991, abandoned, which is a continuation-in-part of Ser. No. 418,832, Oct. 10, 1989, abandoned.

[51] Int. Cl.$^6$ ............................................. C07C 19/08
[52] U.S. Cl. ....................................................... 570/176
[58] Field of Search ............................................ 570/176

[56] References Cited

U.S. PATENT DOCUMENTS

| | | | |
|---|---|---|---|
| 2,494,064 | 1/1950 | Simons et al. | 260/653 |
| 2,615,925 | 10/1952 | Bordner | 260/653 |
| 2,615,926 | 10/1952 | Benning et al. | 260/653 |
| 2,697,124 | 12/1954 | Mantell | 260/653 |
| 2,704,775 | 3/1955 | Clark | 260/653 |
| 2,992,280 | 7/1961 | Olstowski et al. | 260/653 |
| 3,042,727 | 7/1962 | Olstowski et al. | 260/653 |
| 3,439,052 | 4/1969 | Bjornson . | |

FOREIGN PATENT DOCUMENTS

| | | |
|---|---|---|
| 0253410 | 1/1988 | European Pat. Off. . |
| 0305019 | 3/1989 | European Pat. Off. . |
| 1-93549 | 4/1989 | Japan . |
| 698386 | 10/1953 | United Kingdom . |
| 1578933 | 11/1980 | United Kingdom . |

OTHER PUBLICATIONS

Chem Abstracts 111:114734h (1989) Furutaka.

*Primary Examiner*—Alan Siegel

[57] ABSTRACT

Halocarbons such as $CCl_2F_2$, $CF_3CFHCl$ or $CF_3CFCl_2$ which contain chlorine and/or bromine are contacted with hydrogen in the presence of silicon carbide and/or a metal selected from aluminum, molybdenum, titanium, nickel, iron or cobalt (or their alloys) at temperatures of 350° to 700° C. and pressures of 0 to 1000 psig to obtain a product wherein at least one chlorine or bromine in the starting material has been replaced by hydrogen.

20 Claims, No Drawings

HALOCARBON HYDROGENOLYSIS

CROSS-REFERENCE TO RELATED APPLICATION

This application is a continuation of U.S. patent application Ser. No. 08/122,102 filed Sep. 16, 1993 now U.S. Pat. No. 5,364,992, which is a continuation of U.S. patent application Ser. No. 07/847,987 filed Apr. 9, 1992, now abandoned, a national filing of PCT application No. PCT/US90/05637 filed Oct. 9, 1990, which is a continuation-in-part of U.S. patent application Ser. No. 07/418,832 filed Oct. 10, 1989, now abandoned.

BACKGROUND OF THE INVENTION

This invention relates to a process for the hydrogenolysis of halocarbons.

At this time there is a desire to produce halocarbons of reduced chlorine content. Hydrogenolysis is a known method for doing this. For example, see U.K. Patent 1,578,933 which discloses a process for the hydrogenolysis of $CF_3CFHCl$ to $CF_3CH_2F$ using a hydrogenation catalyst, e.g., palladium supported on alumina or carbon. Hydrogenolysis of fluorochlorocarbons by passage through empty tubes made of various materials is also known, e.g., U.S. Pat. No. 2,615,926 discloses platinum tubes, U.S. Pat. No. 2,704,775 discloses nickel or stainless steel tubes and U.S. Pat. No. 3,042,727 discloses a Vycor ® tube.

It is desired to provide a process for converting a halocarbon to a more hydrogenated form with high selectivity and particularly to provide such a process wherein formation of solids and plugging of reaction vessels is minimized.

SUMMARY OF THE INVENTION

We have discovered an improved hydrogenolysis process for reducing the chlorine and/or bromine content of halocarbons. The process may be used for producing saturated halocarbon products such that the yield loss to olefins, coupled by-products, hydrocarbons or fragmented products is less than 10%. The process involves contacting a halocarbon of the formula:

$$C_nH_mF_pX_q$$

wherein
X is Cl or Br,
n is 1 to 10,
m is 0 to 20,
p is 0 to 21,
q is 1 to 22,
provided that m+p+q equals 2n+2 when the compound is acyclic and equals 2n when the compound is cyclic, and provided that when n is 1, q is at least 2, with at least 0.1 mole of hydrogen per mole of halocarbon at a temperature of 350° to 700° C., and a pressure of 0 to 1000 psig, in a reaction vessel (e.g., a tube) of aluminum, molybdenum, titanium, nickel, iron, cobalt, or their alloys, or of silicon carbide, optionally packed with aluminum, molybdenum, titanium, nickel, iron, cobalt or their alloys, or an inert material (e.g., silicon carbide) for a time sufficient to produce a product wherein at least one of X has been replaced by a hydrogen atom. Preferred alloys consist essentially of one or more metals selected from aluminum, molybdenum, titanium, nickel, iron and cobalt, optionally together with chromium and/or tungsten.

The process of the invention provides improved conversions and selectivity and has the further advantage that it does not produce olefins as the major product. Furthermore, the process minimizes the formation of solids fin the reaction vessel, thus permitting long-term operation with less plugging.

DESCRIPTION OF THE INVENTION

An important aspect of the present invention is conducting the hydrogenolysis of halocarbons in the presence of silicon carbide and/or at least one metal selected from aluminum, molybdenum, titanium, nickel, iron, cobalt or their alloys. The metals may be coated on the inside surface of a reaction vessel (e.g., by plating or sputtering the metals or their alloys onto the inside surface). Such coating can help to minimize corrosion of the reaction vessel well. A reaction vessel of these materials (e.g., a metal tube) optionally packed with the metal in suitable form or an inert material such as silica, silicon carbide or low surface area carbon (e.g., shot coke) may also be used. When reference is made to alloys, it is meant a nickel alloy containing from 1 to 99.9% (by weight) nickel, a cobalt alloy containing 1 to 99.9% (by weight) cobalt, an iron alloy containing 0.2 to 99.9% (by weight) iron, a molybdenum alloy containing 70 to 99.9% (by weight) molybdenum, an aluminum alloy containing 80 to 99.9% (by weight) aluminum and a titanium alloy containing 72 to 99.8% (by weight) titanium. Preferably the remainder of these alloys is selected such that the alloy consists essentially of (i) one or more metals selected from aluminum, molybdenum, titanium, nickel, iron and cobalt, and optionally (ii) chromium and/or tungsten.

Most preferred for the practice of this invention are nickel or alloys of nickel such as those containing 52% to 80% nickel, e.g., Inconel ® 600 nickel alloy or Hastelloy ® C276 alloy.

When used for packing, the metal, alloys or inert material may be particles or formed shapes such as, for example, perforated plates, saddles, rings (e.g., Pall ® rings), wire, screen, chips, pipe, shot, gauze and wool. Although an empty reaction vessel (e.g., an empty tube) may be used, the use of this type of packing material can provide the advantage of minimizing backmixing. These types of packing material can also serve as heat transfer materials. In many embodiments, perforated plates, saddles and rings can be especially useful.

The invention is applicable to the hydrogenolysis of halocarbons. The halocarbons can contain 1 to 10 carbon atoms, preferably 1 to 4 carbon atoms, most preferably 1 to 3 carbon atoms. The halocarbons include cyclic as well as acyclic compounds and can be generically represented by the empirical formula $C_nH_mF_pX_q$, where X is Cl and/or Br, preferably Cl, and n is an integer from 1 to 10, m is an integer from 0 to 20, p is an integer from 0 to 21, and q is an integer from 1 to 22, provided that m+p+q=2n+2 when the compound is acyclic and equals 2n when the compound is cyclic. For single carbon compounds (i.e., n is 1) the invention is particularly applicable when q is at least 2.

In a preferred embodiment the halocarbons are represented by the above empirical formula where n=1 to 4, m is 0 to 8, p is 0 to 9, and q is 1 to 9. Preferably, when n is 2 or more, p is at least 1.

The above halocarbons are either commercially available or can be prepared by known methods or adaptation of known methods.

As previously indicated these starting materials when subjected to the process of the invention will result in products wherein one or more X (e.g., chlorine)-has been replaced by hydrogen. Thus the products of the hydrogenolysis reactions of the $C_1$ halocarbons will contain one or two hydrogen atoms, preferably one, and those from $C_2$ compounds from one to three hydrogen atoms, preferably one to two. The $C_3$ halocarbons hydrogenolysis products will contain one to five hydrogen atoms with those containing one to four being preferred. In a similar manner the $C_4$ to $C_{10}$ halocarbon products will contain one or more hydrogen atoms. The preferred process of this invention does not produce olefins as the major product. Instead, the major product of the conversion is a hydrogenolysis product wherein at least one X of the halocarbon starting material has been replaced by a hydrogen atom. This is particularly important for the hydrogenolysis of halocarbons where n is 2 to 10 (i.e., multicarbon halocarbons) where such factors as olefin production can be of concern at temperatures of 350° C. or more. For example, $CF_3CCl_2F$ can be converted with high selectivity to a hydrogenolysis product consisting primarily of $CF_3CHClF$ and $CF_3CH_2F$ with very little olefin formulation. In a preferred embodiment of this invention using halocarbons containing fluorine and chlorine, at least 90% of the hydrogenolysis products contain the same number of fluorines as the original halocarbon. Furthermore the yield loss to olefins, coupled by-products, hydrocarbons, fragmentation products or carbon is less than 10%.

Examples of olefins are products such as $CClF\!=\!CCF_2$ or $CF_2\!=\!CF_2$ the former of which can be obtained from hydrogenolysis of $CCl_2FCClF_2$ and the latter from hydrogenolysis of $CClF_2CClF_2$. An example of a coupled by-product is $CF_3CF\!=\!CFCF_3$ which can be obtained by the hydrogenolysis of $CClF_2CClF_2$. Examples of hydrocarbon products are $CH_4$, $C_2H_6$ and $C_3H_8$ which can be obtained by the hydrogenolysis of $CCl_2F_2$, $CCl_2FCClF_2$ and $CF_3CClFCF_3$ respectively. Examples of fragmentation products are $CF_3H$ and $CH_2F_2$ which can be obtained by the hydrogenolysis of $CF_3CCl_2F$ and its isomer.

The reaction temperature can range from 350° C. to 700° C. Preferably the reaction temperature is at least about 400° C.

The amount of hydrogen contained in the gas stream contacted with the gaseous halocarbon should be at least 0.1 mole per mole of halocarbon. Hydrogen amounts ranging from 0.2 to 5 moles per mole of halocarbon are used for some embodiments. In general, the amount of hydrogen preferably ranges from 0.2 to 60 moles per mole of halocarbon and more preferably ranges from 0.4 to 40 moles per mole of halocarbon. The hydrogen can be fed either in the pure state or diluted with an inert gas, e.g., nitrogen, helium, or argon.

The process pressure is operable over a broad range of pressures. Generally atmospheric (i.e., 0 psig) or superatmospheric pressures of up to 1000 psig are employed. Preferably the pressure is at least about 25 psig.

The extent of the replacement of halogen by hydrogen increases with reaction time. Reaction times between 0.1 minutes and 25 minutes are preferred. Most preferred are reaction times between 0.2 and 8 minutes.

An important feature of the process of the invention is that through selection of the appropriate metal and process conditions, a desired halocarbon hydrogenolysis product can be obtained as the major product with high selectivity and minimal formation of unwanted by-products. Preferably the reaction time and temperature are selected to obtain long term. (>1000 hours) plug free operation and to provide as the major product of the conversion hydrogenolysis product which retains the fluorine content of the starting halocarbon while at least one X is replaced by hydrogen. In many embodiments the reaction time and temperature are controlled so that at least about 90% of halocarbon converted has the same number of fluorine atoms as the halocarbon starting material. Also, in many embodiments the combined yield losses to olefins, coupled by-products, hydrocarbons, or fragmentation products is less than 10%.

An additional desirable feature is that through a selection of an appropriate reaction vessel and packing (e.g., metals, alloys, or inert materials) and process conditions, the products of the hydrogenolysis can contain in high selectivity just one less chlorine or bromine than was present in the starting material. This is particularly useful when q is 2 or more, and it is desired to obtain a major product of the conversion, hydrogenolysis product which contains chlorine and/or bromine. For example, starting with a one-carbon compound containing two or more chlorine or bromine atoms, products containing just one less chlorine or bromine can be obtained in high selectivity.

Although substantial conversions can be achieved in a once-through system, recycle of unreacted halocarbons or intermediates can be employed in a conventional manner. The processes of this invention are considered to be characterized by relativity high activation energies when compared to catalytic hydrogenolysis over conventional Pd/C catalyst. For example, the activation energy for the hydrogenolysis of $CF_3CCl_2F$ over a 0.5% Pd/C catalyst at 167° C. to 200° C. was found to be 14–17 Kcal/mole. The activation energy for the hydrogenolysis of $CF_3CHClF$ over a 0.5%.Pd/C catalyst at 249° C. to 288° C. was found to be 22–28 Kcal/mole. In contrast, the activation energies for the hydrogenolysis reactions of these compounds conducted in the reaction vessels of this invention, either empty or packed, were found to be considerably larger as exemplified in Table A.

TABLE A

| | Activation Energy Data High Temperature Hydrogenolysis | | |
|---|---|---|---|
| Feed | Temp. Range | Packing | Activation Energy |
| F114$_a$[1] | 450–550° C. | — | 49 ± 3 Kcal/mole |
| F114$_x$[2] | 440–600° C. | — | 47 ± 2 |
| F124[3] | 510–600° C. | — | 49 ± 7 |
| F114$_x$ | 400–570° C. | shot coke | 35 ± 1 |
| F114$_x$ | 400–500° C. | nickel screen | 34 ± 3 |
| F124 | 510–570° C. | Inconel ® screen | 41 ± 3 |
| F124 | 520–580° C. | shot coke | 37 ± 1 |

[1]F114$_a$ = $CF_3CCl_2F$
[2]F114$_x$ = Du Pont commercial $CClF_2CClF_2$ containing some $CF_3CCl_2F$
[3]F124 = $CF_3CHClF$ The products of the reaction can be separated and purified by conventional means. The products can be used as solvents, blowing agents, refrigerants and propellants.

Practice of the invention will become further apparent from the following non-limiting examples. In the following Examples the following general procedure was employed, unless otherwise indicated.

General Procedure

A flow reactor under microprocessor control was used. The reactor, unless otherwise indicated, was a 15"×¼" o.d. or ⅜"o.d. Inconel® 600 nickel alloy tube or a 15"×⅜" Hastelloy® C276 nickel alloy tube bent into a U shape and immersed in a heated fluidized sand bath for temperature control. Inconel® 600 is a commercial alloy containing 76% nickel, 15.5% chromium and 8% iron. Hastelloy® C-276 is a commercial alloy containing 59% nickel, 15.5% chromium, 16% molybdenum and 3.75%.tungsten.

The reactor was used either empty or filled with various packing materials as described in the Examples. Hydrogen gas was metered into the system through mass flow controllers. Liquid halocarbons were fed from a syringe pump and vaporized before entering the reactor. Conversions and yields were measured by taking gas stream samples into a gas chromatograph. Product identification was by gc retention times with confirmation by gc-mass spectrometer analysis of samples.

EXAMPLE 1

$CF_3CCl_2F + H_2 \rightarrow CF_3CHClF + CF_3CH_2F$ 2,2-Dichloro-1,1,1,2-tetrafluoroethane (1.47 g/hr) and hydrogen (molar ratio of $H_2/CF_3CCl_2F = 1.9$) were fed into the ¼" empty Inconel® nickel alloy reactor for 38 hours at 450°-550° C. and 250 psig. A sample taken after 14 hours at 550° C. showed an 89% conversion of $CF_3CCl_2F$ with a 65% selectivity to $CF_3CHClF$ and a 32% selectivity to $CF_3CH_2F$. Overall selectivity to the two products was 97%.

EXAMPLE 2

$CF_3CCl_2F + H_2 \rightarrow CF_3CHClF + CF_3CH_2F$ 2,2-Dichloro-1,1,1,2-tetrafluoroethane (1.47 g/hr) and hydrogen (molar ratio of $H_2/CF_3CCl_2F = 1.9$) were fed into the ¼" empty Inconel® nickel alloy reactor for 132 hours at 350°-550° C. and 250 psig. At 350° C. a 2.3% conversion of $CF_3CCl_2F$ with a 76% selectivity to $CF_3CHClF$ and $CF_3CH_2F$ was observed. A sample taken after 20 hours at 500° C. showed an 83% conversion of $CF_3CCl_2F$ with a 98% selectivity to $CF_3CHClF$ and $CF_3CH_2F$.

EXAMPLE 3

$CF_3CHClF + H_2 \rightarrow CF_3CH_2F$

2-Chloro-1,1,1,2-tetrafluoroethane (1.0 g/hr) and hydrogen (molar ratio of $H_2/CF_3CCl_2F = 4.9$) were fed into the ¼" empty Inconel® nickel alloy reactor for 7 hours at 550° C. and 250 psig with average $CF_3CHClF$ conversions of 86% with 98% selectivity to $CF_3CH_2F$ and 0.4% selectivity to $CF_3CH_3$.

EXAMPLE 4

$CF_2Cl_2 + H_2 \rightarrow CF_2HCl$

Dichlorodifluoromethane (9.0 g/hr) and hydrogen (molar ratio of $H_2/CF_2Cl_2 = 1.0$) were fed into the ¼" empty Inconel® nickel alloy reactor as described above for 89 hours at 300 psig, including 79 hours at 500°-550° C. For 12 hours at 500° C. during this run, at a mean age of 64 synthesis hours, the average conversion of $CF_2Cl_2$ was 26%.

EXAMPLE 5

$CF_3CClFCF_3 + H_2 \rightarrow CF_3CHFCF_3$

2-Chloroheptafluoropropane (1.5 g/hr) and hydrogen (22 cc/min) were fed into the ¼" empty Inconel® nickel alloy reactor for 3 hours at 450° C. and 250 psig with 30–40% conversion and a 98% selectivity to $CF_3CHFCF_3$.

EXAMPLE 6

$CF_3CClFCF_3 + H_2 \rightarrow CF_3CHFCF_3$

2-Chloroheptafluoropropane (1.38 g/hr) and hydrogen (22 cc/min) were fed into the ¼" Inconel® nickel alloy reactor filled with Inconel® nickel alloy chips (10 g). Operation at 500° C. and 250 psig for 33.3 hours gave an average of 91.3% conversion with 99.4% selectivity to $CF_3CHFCF_3$.

EXAMPLE 7

$CF_3CCl_2F + H_2 \rightarrow CF_3CHClF + CF_3CH_2F$ 2,2-Dichloro-1,1,1,2-tetrafluoroethane (2.9 or 5.9 g/hr) and hydrogen (molar ratio of $H_2/CF_3CCl_2F = 2.2$ or 4.3) were fed into the ⅜" Inconel® nickel alloy reactor filled with Inconel® nickel alloy wool (7.96 g) for 106 hours at 400°-500° C. and 250 psig. The average conversion of $CF_3CCl_2F$ over the whole period was 99.9%. For a 12-hour period at 450° C. with a $CF_3CCl_2F$ feed rate of 5.9 g/hr (molar ratio $H_2/CF_3CCl_2F=4.3$) the following average selectivities were observed: 69% $CF_3CHClF$ and 26% $CF_3CH_2F$.

EXAMPLE 8

$CF_3CHClF + H_2 \rightarrow CF_3CH_2F$

2-Chloro-1,1,1,2-tetrafluoroethane (5.5 g/hr) and hydrogen (molar ratio of $H_2/CF_3CHClF = 1.1$) were fed into the ⅜" Inconel® nickel alloy reactor filled with a pure nickel screen (8.77 g), operated at various feed rates and a pressure of 300 psig. With a $CF_3CHClF$ feed rate of 5.48 g/hr and hydrogen (molar ratio of $H_2/CF_3CHClF=1.1$) conversion at 525° C. and an average synthesis time of 82 hours averaged 47% with 98% selectivity to $CF_3CH_2F$ for 12 hours. At an average synthesis time of 644 hours conversion averaged 39% with 97% selectivity to $CF_3CH_2F$. At 1181 synthesis hours the operating pressure was increased to 500 psig. Conversion of $CF_3CHClF$ averaged 68% for 14 hours with a selectivity to $CF_3CH_2F$ of 98%.

EXAMPLE 9

$CF_3CHClF + H_2 \rightarrow CF_3CH_2F$

2-Chloro-1,1,1,2-tetrafluoroethane (2.7 or 5.5 g/hr) and hydrogen (molar ratio of $H_2/CF_3CHClF=1.9$) were fed into the ⅜" Inconel® nickel alloy reactor filled with Inconel® nickel alloy wool (7.96 g) for 23 hours at 400°-500° C. and 250 psig. Between 18 and 23 hours, at 400° C. with a $CF_3CHClF$ feed rate of 2.7 g/hr, the average conversion was 23% and the selectivity to $CF_3CH_2F$ was 82%.

EXAMPLE 10

$CF_2Cl_2 + H_2 \rightarrow CF_2HCl$

Dichlorodifluoromethane (4.5 or 33.0 g/hr) and hydrogen (molar ratio of $H_2/CF_2Cl_2 = 1$ or 0.5) were fed into the ⅜" Inconel® nickel alloy reactor filled with pure nickel screen (17.5 g) for 135 hours at 300 psig. For 12 hours at 450° during this run, at a mean synthesis time of 78 hours, with a CF$_2$Cl$_2$ feed rate of 4.5 g/hr (molar ratio H$_2$/CF$_2$Cl$_2$=1.0), the average conversion of CF$_2$Cl$_2$ was 34%.

EXAMPLE 11

CF$_3$CClF$_2$+H$_2$→CF$_3$CHF$_2$

Chloropentafluoroethane vapor (6 cc/min) and hydrogen (5 cc/min) were fed into a Hastelloy ® nickel alloy reactor (6"×⅜" O.D.) filled with pure nickel screen (39.68 g) at 550° C. and atmospheric pressure. The reaction products were analyzed with the following results: 59% conversion of CF$_3$CClF$_2$ with a 97% selectivity to CF$_3$CHF$_2$.

EXAMPLE 12

CF$_3$CClF$_2$+H$_2$→CF$_3$CHF$_2$

Chloropentafluoroethane vapor (5 cc/min) and hydrogen (6 cc/min) were fed into an Inconel ® nickel alloy reactor (6"×⅜" O.D.) filled with pure nickel screen (51.98 g) at 550° C. and atmospheric pressure. The reaction products were analyzed with the following results: 65% conversion of CF$_3$CClF$_2$ with a 95% selectivity to CF$_3$CHF$_2$.

The reaction was run under the same conditions as described above, except that the feed rates were changed to CF$_3$CClF$_2$ (5 cc/min) and H$_2$ (12 cc/min). The reaction products were analyzed with the following results: 62% conversion of CF$_3$CClF$_2$ with an 86% selectivity to CF$_3$CHF$_2$.

EXAMPLE 13

CClF$_2$CClF$_2$/CF$_3$CCl$_2$F+H$_2$→CHF$_2$CClF$_2$/CF$_3$CHClF+CHF$_2$CHF$_2$/CF$_3$CH$_2$F

A vapor mixture of CClF$_2$CClF$_2$(9)/CF$_3$CCl$_2$F(1) (5 cc/min) and hydrogen (6 cc/min) was fed into a Hastelloy ® nickel alloy reactor (6"×⅜" O.D.) filled with pure nickel screen (39.68 g) at 550° C. and atmospheric pressure. The reaction products were analyzed with the following results: 61% conversion of CClF$_2$CClF$_2$/CF$_3$CCl$_2$F with a 46% selectivity to CHF$_2$CClF$_2$/CF$_3$CHClF and a 34% selectivity to CHF$_2$CHF$_2$/CF$_3$CH$_2$F.

EXAMPLE 14

CF$_3$CCl$_2$F+H$_2$→CF$_3$CHClF+CF$_3$CH$_2$F 2,2-Dichlorotetrafluoroethane vapor (5 cc/min) and hydrogen (6 cc/min) were fed into an Inconel ® nickel alloy reactor (6"×⅜" O.D.) filled with pure nickel screen (51.98 g) at 550° C. and atmospheric pressure. The reaction products were analyzed with the following results: 83% conversion of CF$_3$CCl$_2$F with a 5% selectivity to CF$_3$CHClF and a 66% selectivity to CF$_3$CH$_2$F.

EXAMPLE 15

CF$_3$CHClF+H$_2$→CF$_3$CH$_2$F

2-Chloro-1,1,1,2-tetrafluoroethane vapor (5 cc/min) and hydrogen (6 cc/min) were fed into an Inconel ® nickel alloy reactor (6"×⅜" O.D.) filled with pure nickel screen (51.98 g) at 550° C. and atmospheric pressure. The reaction products were analyzed with the following results: 58% conversion of CF$_3$CHClF with an 85% selectivity to CF$_3$CH$_2$F.

EXAMPLE 16

CClF$_2$CCl$_2$F+H$_2$→CHClFCClF$_2$+CHClFCHF$_2$ 1,1,2-Trichloro-1,2,2-trifluoroethane (3.13 g/hr) and hydrogen (molar ratio=4.75) were fed into the ⅜" Inconel ® nickel alloy U-tube reactor as described in the general procedure, with the exit leg filled with pure nickel screen (8 g), at 450° C. and 500 psig. Over a 6-hour period the reaction products were analyzed with the following results: 81% conversion of CCl$_2$FCClF$_2$ with 96% combined selectivity to C$_2$H$_3$F$_3$, C$_2$H$_2$ClF$_3$, and C$_2$HCl$_2$F$_3$. Selectivity to CClF=CF$_2$ was 2%. When the temperature was raised to 475° C. for 7 hours, the average conversion of CCl$_2$FCClF$_2$ was 97% with 95% combined selectivity to C$_2$H$_3$F$_3$, C$_2$H$_2$ClF$_3$, and C$_2$HCl$_2$F$_3$. Selectivity to CClF=CF$_2$ was 1%.

EXAMPLE 17

CF$_3$CHClF+H$_2$→CF$_3$CH$_2$F

2-Chloro-1,1,1,2-tetrafluoroethane (2.7 g/hr) and hydrogen (molar ratio of H$_2$/CF$_3$CHClF=0.2) were fed into an empty 6"×⅜" O.D. Hastelloy ® C276 nickel alloy reactor for 8 hours at 535° C. and 300 psig. The average conversion of CF$_3$CHClF was 22% with an average 97% CF$_3$CH$_2$F selectivity.

EXAMPLE 18

CF$_3$CHClF+H$_2$→CF$_3$CH$_2$F

2-Chloro-1,1,1,2-tetrafluoroethane (2.7 g/hr) and hydrogen (molar ratio of H$_2$/CF$_3$CHClF=1.5) were fed into 6"×⅜" O.D. Hastelloy ® C276 nickel alloy reactor containing 14/20 mesh acid-washed SiC (6.5 g) for 60 hours at 535° C. and 300 psig. The average conversion of CF$_3$CHClF was 75% with an average 97% CF$_3$CH$_2$F selectivity.

EXAMPLE 19

CF$_3$CHClF+H$_2$→CF$_3$CH$_2$F

2-Chloro-1,1,1,2-tetrafluoroethane and hydrogen were fed at various rates over 113 hours into the ⅜" Hastelloy ® C276 nickel alloy tube operated at 300 psig and containing Conoco Shot coke (9.2 grams, 10 cc), a highly fused petroleum coke with a surface area of 0.5 sq m/g. For an 8-hour period at 560° C. and an average time in synthesis of 102 hours, with a CF$_3$CHClF feed rate of 11.0 g/hr and a hydrogen feed rate of 32 cc/min (molar ratio of H$_2$/CF$_3$CHClF=1) the average conversion of CF$_3$CHClF was 13% with an average selectivity to CF$_3$CH$_2$F of 99%.

EXAMPLE 20

CClF$_2$CClF$_2$+H$_2$→CHF$_2$CClF$_2$+CHF$_2$CHF$_2$

Commercial 1,2-dichloro-1,1,2,2-tetrafluoroethane, containing 9% (molar) 1,1-dichloro-1,2,2,2-tetrafluoroethane, and hydrogen were fed at various rates over 150 hours into the ⅜" Inconel ® nickel alloy tube operated at 300 psig and containing Conoco Shot coke (9.2 grams, 10 cc), a highly fused petroleum coke with a surface area of 0.5 sq. m/g. For a 16-hour period at 550° C. and an average time in synthesis of 59 hours, with a CClF$_2$CClF$_2$ feed rate of 5.9 g/hr and a hydrogen feed rate of 28 cc/min (molar ratio of H$_2$/CClF$_2$CClF$_2$=2) the average conversion of the C$_2$Cl$_2$F$_4$ isomers was 84% with an average selectivity to $CHF_2CClF_2$ and its isomer of 49%, and an average selectivity to $CHF_2CHF_2$ and its isomer of 47%.

EXAMPLE 21

$$CF_3CCl_2F + H_2 \rightarrow CF_3CHClF + CF_3CH_2F$$

2,2-Dichloro-1,1,1,2-tetrafluoroethane (2 mL/h), which was vaporized before being mixed with hydrogen (13 cc/min), was fed into a Hastelloy ® C nickel alloy reactor (6"×⅜" O.D.) as described above, containing Conoco Shot coke (14.0 grams, 10 mesh), a highly fused petroleum coke with a surface area of 0.5 sq m/g at 550° C. and 100 psig. After 28 hours of operation, product analysis indicated that $CF_3CCl_2F$ conversion was quantitative and selectivity to $CF_3CHClF$ and $CF_3CH_2F$ was 64.7% and 33.3% respectively.

EXAMPLE 22

$$CF_3CClF_2 + H_2 \rightarrow CF_3CHF_2$$

Chloropentafluoroethane vapor (10 cc/min) and hydrogen (10 cc/min) were fed into a Hastelloy ® C nickel alloy reactor (6"×⅜" O.D.) as described above, charged with Conoco Shot coke (14.0 grams, 10 mesh), a highly fused petroleum coke with a surface area of 0.5 sq m/g at 550° C. After 10 hours of operation, product analysis indicated that $CF_3CClF_2$ conversion was 7.5% and selectivity to $CF_3CHF_2$ was 94.7%.

This experiment was substantially repeated except that the $CF_3CClF_2$ flow was 5 cc/min and the hydrogen flow was 6 cc/min. Product analysis indicated that $CF_3CClF_2$ conversion was 13.3% and selectivity to $CF_3CHF_2$ was 89.6%.

EXAMPLE 23

$$CClF_2CClF_2 + H_2 \rightarrow CHF_2CClF_2 + CHF_2CHF_2$$

Commercial 1,2-dichloro-1,1,2,2-tetrafluoroethane, containing 9% (molar) 1,1-dichloro-1,2,2,2-tetrafluoroethane, and hydrogen were fed at various rates for 172 hours into an empty 15"×⅜" O.D. Hastelloy ® C276 nickel alloy tube, as described above, operated at 500 psig. For a 13 hour period at 500° C. and an average time in synthesis of 66 hours, with a $CClF_2CClF_2$ feed rate of 5.9 g/hr and hydrogen feed rate of 10 cc/min (molar ratio of $H_2/CClF_2CClF_2=0.7$) the average conversion of $C_2Cl_2F_4$ isomers was 58% with an average selectivity to $CHF_2CClF_2$ and its isomer of 75% and an average selectivity to $CHF_2CHF_2$ and its isomer of 24%. For a 9 hour period at 500° C. and an average time in synthesis of 148 hours, with a $CClF_2CClF_2$ feed rate of 1.47 g/hr and a molar feed ratio of $H_2/CClF_2CClF_2$ of 1.5 the average conversion of $C_2Cl_2F_4$ isomers was 88% with an average selectivity of $CHF_2CClF_2$ and its isomer of 45% and an average selectivity to $CHF_2CHF_2$ and its isomer of 54%.

EXAMPLE 24

$$CClF_2CClF_2 + H_2 \rightarrow CHF_2CClF_2 + CHF_2CHF_2$$

Commercial 1,2-dichloro-1,1,2,2-tetrafluoroethane, containing 9% (molar) 1,1-dichloro-1,2,2,2-tetrafluoroethane, and hydrogen were fed at various rates for 192 hours into a 15"×⅜" O.D. Inconel ® 600 nickel alloy tube, as described above, containing 8.0 g of 24×100 mesh nickel screen and operated at 500 psig. For a 10 hour period at 400° C. and a $CClF_2CClF_2$ feed rate of 0.7 g/hr and hydrogen feed rate of 1.7 cc/min (molar ratio of $H_2/CClF_2CClF_2=1$); the average conversion of $C_2Cl_2F_4$ isomers was 61% with an average selectivity to $CHF_2CClF_2$ and its isomer of 77.0% and an average selectivity to $CHF_2CHF_2$ and its isomer of 22.7%.

EXAMPLE 25

$$CF_3CCl_2F + H_2 \rightarrow CF_3CHClF + CF_3CH_2F$$

2,2-Dichloro-1,1,1,2-tetrafluoroethane and hydrogen were fed at various rates for 68 hours to an empty Hastelloy ® C276 nickel alloy tube, as described above, operated at 500 psig. For a five hour period at 500° C. and an average time in synthesis of 41 hours, with a $CF_3CCl_2F$ feed rate of 5.9 g/hr and a hydrogen rate of 14 cc/min (molar ratio of $H_2/CF_3CCl_2F=1$), the average conversion was 64% with an average selectivity to $CF_3CHClF$ of 83.6 and an average selectivity of $CF_3CH_2F$ of 15.6%.

EXAMPLE 26

$$CClF_2CClF_2 + H_2 \rightarrow CHF_2CClF_2 + CHF_2CHF_2$$

Chrome-Plated Reactor

Commercial 1,2-dichloro-1,1,2,2 tetrafluoroethane, containing 9% (molar) 1,1-dichloro-1,2,2,2-tetrafluoroethane, and hydrogen were fed at various rates over 55 hours into a 15"×¼" o.d. empty chrome-plated U-tube reactor, as described above, operated at 300 psig. For a 20-hour period at 500° C. and an average time in synthesis of 16 hours, with a $CClF_2CClF_2$ feed rate of 2.9 g/hr and a hydrogen feed rate of 13.3 cc/min (molar ratio $H_2/CClF_2CClF_2=2$); the average conversion of the $CClF_2CClF_2$ isomers was 56% with an average selectivity to $CHF_2CClF_2$ and its isomer of 21%, and an average selectivity to $CHF_2CHF_2$ and its isomer of 76%.

EXAMPLE 27

$$CClF_2CClF_2 + H_2 \rightarrow CHF_2CClF_2 + CHF_2CHF_2$$

Aluminum Reactor

Commercial 1,2-dichloro-1,1,2,2-tetrafluoroethane, containing 9% (molar) 1,1-dichloro-2,2,2,2 tetrafluoroethane, and hydrogen were fed at various rates over 31 hours into an empty 15"×¼" o.d. aluminum U-tube reactor, as described above, operated at 50 psig. For a 3-hour period at 500° C. and an average time in synthesis of 28 hours, with a $CClF_2CClF_2$ feed rate of 1.47 g/hr and a hydrogen feed rate of 7.0 cc/min (molar ratio $H_2/CClF_2CClF_2=2$); the average conversion of the $CClF_2CClF_2$ isomers was 5% with an average selectivity to $CHF_2CClF_2$ and its isomer of 49%, and an average selectivity to $CHF_2CHF_2$ and its isomers of 33%.

EXAMPLE 28

$$CClF_2CClF_2 + H_2 \rightarrow CHF_2CClF_2 + CHF_2CHF_2$$

Titanium Reactor

Commercial 1,2-dichloro-1,1,2,2 tetrafluoroethane, containing 9% (molar) 1,1-dichloro-1,2,2,2-tetrafluoroethane, and hydrogen were fed at various rates over 42 hours into a 15"×¼" o.d. empty titanium U-tube reactor, as described above, operated at 50 psig. For a 17-hour period at 500° C. and an average time in synthesis of 9.5 hours, with a $CClF_2CClF_2$ feed rate of 2.9 g/hr and a hydrogen feed rate of 13.9 cc/min (molar ratio $H_2/CClF_2CClF_2=2$) the average conversion of the $CClF_2CClF_2$ isomers was 14.2% with an average selectivity to $CHF_2CClF_2$ and its isomer of 57%, and an average selectivity to $CHF_2CHF_2$ and its isomer of 24.4%.

EXAMPLE 29

$CF_3CHClF + H_2 \rightarrow CF_3CH_2F$

Silicon Carbide Reactor

2-Chloro-1,1,1,2 tetrafluoroethane and hydrogen were fed at various rates over 47 hours into a 15"×¼" o.d. empty silicon carbide straight tube reactor, as described above, operated at 0 psig. For a 12-hour period at 600° C. and an average time in synthesis of 29 hours, with a $CF_3CHClF$ feed rate of 2.74 g/hr and a hydrogen feed rate of 8.2 cc/min (molar ratio $H_2/CF_3CHClF=1$); the average conversion of the $CF_3CHClF$ was 4.3%, with an average selectivity to $CF_3CH_2F$ of 89.7%.

EXAMPLE 30

$CF_3CCl_2F + H_2 \rightarrow CF_3CHClF + CF_3CH_2F$

Silicon Carbide Reactor 2,2-Dichloro-1,1,1,2-tetrafluoroethane 2.94 g/hr were fed into a silicon carbide straight tube reactor, as described above, with 6.4 cc/min of hydrogen (molar ratio $H_2/CF_3CCl_2F=1$) operated at 0 psig for 41 hours. Over a 15-hour period at 500° C. and an average time in synthesis of 27 hours; the average conversion of $CF_3CCl_2F$ was 23% with an average selectivity to $CF_3CHClF$ of 54% and an average selectivity to $CF_3CH_2F$ of 0.6%.

EXAMPLE 31

$CClF_2CClF_2 + H_2 \rightarrow CHF_2CClF_2 + CHF_2CHF_2$

Silicon Carbide Reactor

Commercial 1,2-dichloro-1,1,2,2 tetrafluoroethane, containing 9% (molar) 1,1-dichloro-1,2,2,2 tetrafluoroethane, and hydrogen were fed at various feed rates over 38 hours into a straight tube silicon carbide reactor tube, as described above, operated at 0 psig. For a 12-hour period at 575° C. and at an average time in synthesis of 14 hours, with a feed rate of 13.9 cc/min of hydrogen and 2 grams/hr of $CClF_2CClF_2$ (molar ratio $H_2/CClF_2CClF_2=2$); the average conversion of the $CClF_2CClF_2$ isomers was 35.6% with an average selectivity to $CHF_2CClF_2$ and its isomers of 28% and an average selectivity to $CHF_2CHF_2$ and its isomers of 27%.

EXAMPLE 32

$CF_2Cl_2 + H_2 \rightarrow CF_2HCl + CH_2F_2$

Silicon Carbide Reactor

Dichlorodifluoromethane (2.6 g/hr) and hydrogen (molar ratio $H_2/CF_2Cl_2=1.0$) were fed into an empty ¼"×15" silicon carbide straight tube reactor, as described above, over a 28-hour period. For four hours at 575° C. during this run, at an average synthesis time of 26 hours; the average conversion of $CF_2Cl_2$ was 35.6%.

EXAMPLE 33

$CF_3CCl_3 + H_2 \rightarrow CF_3CHCl_2 + CF_3CH_2Cl$

Hastelloy ® Nickel Alloy Reactor 1,1,1-Trichloro-2,2,2-trifluoroethane and hydrogen were fed into an empty 15"×⅜" Hastelloy ® C276 nickel alloy U-tube reactor, as described above, at 300 psig for a period of 28 hours. Over a 6-hour period at 425° C. and 300 psig, at an average time in synthesis of 17 hours, with a feed rate of $CF_3CCl_3$ of 6.25 g/hr and a hydrogen feed rate of 14.0 sccm (molar ratio $H_2/CF_3CCl_3=1.0$); the average conversion of $CF_3CCl_3$ was 33% with a selectivity to $CF_3CHCl_2$ of 95% and a selectivity to $CF_3CH_2Cl$ of 5%.

EXAMPLE 34

$CCl_4 + H_2 \rightarrow CHCl_3 + CH_2Cl_2$

Inconel ® Nickel Alloy Reactor

Carbon tetrachloride (6.57 g/hr) and hydrogen (200 sccm) were fed into an empty 15"×¼" Inconel ®600 nickel alloy U-tube reactor, as described above, operated at pressures between 0 psig and 300 psig for 149 hours. For a 10-hour period at 457° C. and 300 psig and an average time in synthesis of 136 hours, with a $CCl_4$ feed rate of 6.57 g/hr and a hydrogen feed rate of 200 sccm (molar ratio $H_2/CCl_4=12$); the average conversion of $CCl_4$ was 45% with an average selectivity to $CHCl_3$ of 59% and an average selectivity to $CH_2Cl_2$ of 2.8%.

EXAMPLE 35

$CF_3CHClF + H_2 \rightarrow CF_3CH_2F$

High Hydrogen Ratio

2-Chloro-1,1,1,2-tetrafluoroethane and hydrogen were fed at varying rates for over 48 hours to a 56" ×¼" Inconel ® 600 nickel alloy coil reactor at 300 psig and temperatures between 550° and 600° C. For 4 hours at 600° C. at an average time in synthesis of 39 hours, with a $CF_3CHClF$ feed rate of 1.6 mL/hr and a $H_2$ feed rate of 130 sccm ($H_2/CF_3CHClF$ mol ratio=20) the average conversion of $CF_3CHClF$ was 83% and the selectivity to $CF_3CH_2F$ was 94%. At a lower $H_2$ flow of 65 sccm and the same $CF_3CHClF$ feed rate and temperature ($H_2/CF_3CHClF$ mol ratio=10) the average conversion of $CF_3CHClF$ over a 5-hour period was 90% with a 94% selectivity to $CF_3CH_2F$.

EXAMPLE 36

$CF_3CHClF + H_2 \rightarrow CF_3CH_2F$

High Hydrogen Ratio

2-Chloro-1,1,1,2-tetrafluoroethane and hydrogen were fed at various rates for 1207 hours into a 15"×⅜" Inconel ® 600 nickel alloy U-tube, packed with 8.77 g 150 mesh nickel screen, and operated at various temperatures at 300 psig. For a 23-hour period at 550° C. and an average time in synthesis of 755 hours with a $CF_3CHClF$ feed rate of 0.4 ml/hour and a hydrogen feed rate of 18 sccm/min (molar ratio $H_2/CF_3CHClF=11$), the average conversion of $CF_3CHCl$ was 99.6% with a selectivity to $CF_3CH_2F$ of 93%.

EXAMPLE 37

$CCl_2FCF_3 + H_2 \rightarrow CHClFCF_3 + CH_2FCF_3$

High Hydrogen Ratio 1,1-Dichloro-1,2,2,2-tetrafluoroethane and hydrogen were fed at various rates for 237 hours into a 15"×⅜" Hastelloy ® C nickel alloy U-tube packed with 9.29 g of Conoco shot coke and operated at various temperatures at 300 psig. For a 5-hour period at 575° C. and an average time in synthesis of 227 hours with a $CCl_2FCF_3$ feed rate of 36 mL/hr and a hydrogen feed rate of 50 sccm/min (molar ratio H$_2$/CCl$_2$FCF$_3$=40), the average conversion of CCl$_2$FCF$_3$ was 100%. The selectivity to CHClFCF$_3$ was 32% and the selectivity to CH$_2$FCF$_3$ was 59%.

EXAMPLE 38

CF$_3$CClF$_2$+H$_2$→CF$_3$CHF$_2$

2-Chloro-1,1,1,2,2-pentafluoroethane and hydrogen were fed at various rates to 15"×⅜" Hastelloy ® C276 nickel alloy U-tube operated at 300 psig and various temperatures for 136 hours. For 10 hours, at an average time in synthesis of 58 hours and a temperature of 575° C., with a CF$_3$CClF$_2$ feed rate of 2.1 g/hr and a hydrogen feed rate of 14.0 sccm (molar ratio H$_2$/CF$_3$CClF$_2$=2.5), the conversion of CF$_3$CClF$_2$ was 89.5% and the selectivity to CF$_3$CHF$_2$ was 99.9%.

For an 8-hour period at an average time in synthesis of 131 hours and a temperature of 575° C., with a feed rate of CF$_3$CClF$_2$ of 4.15 g/hr and a hydrogen feed rate of 329 sccm (molar ratio H$_2$/CF$_3$CClF$_2$=30), the average conversion of CF$_3$CClF$_2$ was 39% with a selectivity to CF$_3$CHF$_2$ was 99.6%.

Particular embodiments of the invention are included in the examples. Other embodiments will become apparent to those skilled in the art from a consideration of the specification or practice of the invention disclosed herein. It is understood that modifications and variations may be practiced without departing from the spirit and scope of the novel concepts of this invention. It is further understood that the invention is not confined to the particular formulations and examples herein illustrated, but it embraces such modified forms thereof as come within the scope of the following claims.

What is claimed is:

1. A process for the hydrogenolysis of a halocarbon starting compound of the formula C$_n$H$_m$F$_p$X$_q$, wherein X is Cl or Br, n is 2 to 10, m is 0 to 20, p is 0 to 21, and q is 1 to 22, provided that m+p+q equals 2n+2 when the compound is acyclic and equals 2n when the compound is cyclic, comprising:

contacting said halocarbon starting compound with at least 0.1 mole of hydrogen per mole of said halocarbon starting compound in an empty reaction vessel of nickel to its alloys at a pressure within the range of from 0 psig to 1000 psig, at a temperature within the range of from 350° C. to 700° C. and for a time sufficient to produce a saturated product wherein at least one X has been replaced by hydrogen.

2. The process of claim 1 wherein the temperature ranges from 400° C. to 700° C. and the pressure is 0 to 500 psig.

3. The process of claim 1 wherein X is Cl; n is 2 to 4, m is 0 to 8, p is 0 to 9 and q is 1 to 9.

4. The process of claim 2 wherein the halocarbon starting compound is selected from the group CF$_3$CCl$_3$ and CF$_3$CClF$_2$; and wherein at least 90% of the product of said hydrogenolysis contains the same number of fluorine substituents as said halocarbon starting compound.

5. The process of claim 1 wherein the halocarbon starting compound is selected from the group consisting of CF$_3$CCl$_2$F, CF$_3$CHClF, CF$_3$CClFCF$_3$, CClF$_2$CClF$_2$, CF$_3$CCl$_3$ and CF$_3$CClF$_2$; and wherein less than 10% olefinic by-product is produced.

6. The process of claim 5 wherein CCl$_2$FCClF$_2$ is reacted with hydrogen and C$_2$ClF$_3$ by-product is produced.

7. The process of claim 5 wherein CClF$_2$CClF$_2$ is reacted with hydrogen and C$_2$F$_4$ by-product is produced.

8. The process of claim 1 wherein the halocarbon starting compound is selected from the group consisting of CF$_3$CCl$_2$F, CF$_3$CHClF, CF$_3$CClFCF$_3$, CClF$_2$CClF$_2$, CF$_3$CCl$_3$ and CF$_3$CClF$_2$; and wherein less than 10% coupled by-product is produced.

9. The process of claim 8 wherein CClF$_2$CClF$_2$ is the halocarbon starting material.

10. The process of claim 8 wherein CClF$_2$CClF$_2$ is reacted with hydrogen and CF$_3$CF=CFCF$_3$ by-product is produced.

11. The process of claim 1 wherein n is 3 and wherein the hydrogenolysis product contains from 1 to 4 hydrogen substituents.

12. The process of claim 1 wherein the halocarbon starting compound is selected from the group consisting of CF$_3$CCl$_2$F, CF$_3$CHClF, CF$_3$CClFCF$_3$, CClF$_2$CClF$_2$, CF$_3$CCl$_3$ and CF$_3$CClF$_2$; and wherein less than 10% of hydrocarbons are produced.

13. A process for the hydrogenolysis of a halocarbon starting compound of the formula C$_n$H$_m$F$_p$Cl$_q$, wherein n is 2 to 4, m is 0 to 8, p is 0 to 9, and q is 1 to 9, provided that m+p+q equals 2n+2 when the compound is acyclic and equals 2n when the compound is cyclic, comprising:

contacting said halocarbon starting compound with at least 0.1 mole of hydrogen per mole of said halocarbon starting compound in an empty reaction vessel of nickel or its alloys at a pressure, a temperature and a time sufficient to produce a saturated product wherein at least one chlorine has been replaced by hydrogen at an activation energy of about 47 Kcal/mole or more, at least 90% of the product of said hydrogenolysis being a saturated product containing the same number of fluorine substituents as the halocarbon starting compound.

14. The process of claim 13 wherein the halocarbon starting material is selected from the group consisting of CClF$_2$CClF$_2$, CCl$_2$FCF$_3$ and CHClFCF$_3$.

15. A process for the hydrogenolysis of a halocarbon starting compound of the formula C$_n$H$_m$F$_p$X$_q$, wherein X is Cl or Br, n is 2 to 4, m is 0 to 8, p is 0 to 9, and q is 1 to 9, provided that m+p+q equals 2n+2 when the compound is acyclic and equals 2n when the compound is cyclic, comprising:

contacting said halocarbon starting compound with at least 0.1 mole of hydrogen per mole of said halocarbon starting compound in a reaction vessel of nickel or its alloys which is packed with formed shapes of aluminum, molybdenum, nickel, cobalt, or their alloys, at a pressure within the range of from 0 psig to 1000 psig, at a temperature within the range of from 500 C. to 700 C. and for a time sufficient to produce a product wherein at least one X has been replaced by hydrogen; at least 90% of the product of said hydrogenolysis being a saturated product containing the same number of fluorine substituents as the halocarbon starting material.

16. The process of claim 15 wherein said packing is in the form of perforated plates, saddles or rings.

17. The process of claim 16 wherein said packing is in the form of perforated plates.

18. The process of claim 16 wherein the packing is of nickel or a nickel alloy.

19. The process of claim 15 wherein the halocarbon starting compound is selected from the group consisting of CF$_3$CClFCF$_3$, CF$_3$CCl$_2$F, CF$_3$CHClF, CClF$_2$CClF$_2$, CHF$_2$CClF$_2$, C$_2$F$_5$Cl, CClF$_2$CCl$_2$F, CF$_3$CCl$_3$, CCl$_2$FCCl$_2$F and CClF$_2$CCl$_3$.

20. The process of claim 15 wherein the halocarbon starting material is selected from the group consisting of CClF$_2$CF$_3$, CCl$_2$FCF$_3$, and CCl$_3$CF$_3$.

* * * * *

UNITED STATES PATENT AND TRADEMARK OFFICE
CERTIFICATE OF CORRECTION

PATENT NO. : 5,430,204

DATED : JULY 4, 1995

INVENTOR(S) : William H. Manogue, Mallikarjuna Rao

It is certified that error appears in the above-identified patent and that said Letters Patent is hereby corrected as shown below:

Col. 2, line 8, change: "solids fin the" to:
-- solids in the --.

Col. 2, line 14, change: "ed-from" to: -- ed from --.

Col. 3, line 6, change: "chlorine)-has" to
-- chlorine) has --.

Col. 5, line 61, change "$CF_2C_{12}$" to -- $CF_2Cl_2$ --.

Col. 13, line 46, change "nickel to its" to
-- nickel or its --.

UNITED STATES PATENT AND TRADEMARK OFFICE
CERTIFICATE OF CORRECTION

PATENT NO. : 5,430,204
DATED : JULY 4, 1995
INVENTOR(S) : William H. Manogue, Mallikarjuna Rao It is certified that error appears in the above-indentified patent and that said Letters Patent is hereby corrected as shown below:

Col. 13, line 59, please add, after "group" -- consisting of $CF_3CCl_2F$, $CF_3CHClF$, $CF_3CClFCF_3$, $CClF_2CClF_2$, --.

Signed and Sealed this

Twenty-seventh Day of August, 1996

Attest:

BRUCE LEHMAN

Attesting Officer

Commissioner of Patents and Trademarks